United States Patent [19]

Vrudhula et al.

[11] Patent Number: 6,096,762
[45] Date of Patent: Aug. 1, 2000

[54] NEUROTROPHIC DIFLUOROAMIDE AGENTS

[75] Inventors: Vivekananda M. Vrudhula, Killingworth; Gene M. Dubowchik, Middlefield; Bireshwar Dasgupta, Middletown; Dolatrai M. Vyas, Madison, all of Conn.

[73] Assignee: Bristol-Myers Squibb Company, Princeton, N.J.

[21] Appl. No.: 09/316,792

[22] Filed: May 21, 1999

Related U.S. Application Data

[60] Provisional application No. 60/087,642, Jun. 2, 1998.

[51] Int. Cl.[7] .................. A61K 31/166; C07C 225/10; C07C 59/347
[52] U.S. Cl. ................... 514/318; 560/41; 562/459; 562/463; 562/568; 564/209; 514/354; 514/449; 514/538; 514/549; 514/550; 546/226; 546/194; 546/279.1; 548/533
[58] Field of Search ................... 562/459, 463, 562/568; 514/628, 449, 538, 549, 550, 423, 318, 354; 564/209; 560/41; 548/533; 546/226, 194, 279.1

[56] References Cited

U.S. PATENT DOCUMENTS

| | | | |
|---|---|---|---|
| 4,873,221 | 10/1989 | Trainor | 514/18 |
| 5,045,537 | 9/1991 | Weidmann | 514/63 |
| 5,192,773 | 3/1993 | Armistead et al. . | |
| 5,330,993 | 7/1994 | Armistead et al. . | |
| 5,516,797 | 5/1996 | Armistead et al. . | |
| 5,622,970 | 4/1997 | Armistead et al. . | |
| 5,654,332 | 8/1997 | Armistead . | |
| 5,696,135 | 12/1997 | Steiner et al. . | |
| 5,721,256 | 2/1998 | Hamilton et al. . | |
| 6,031,121 | 2/2000 | Suzuki et al. | 558/254 |

FOREIGN PATENT DOCUMENTS

| | | |
|---|---|---|
| 405994A2 | 1/1991 | European Pat. Off. . |
| 564924B1 | 10/1993 | European Pat. Off. . |
| WO92/19593 | 11/1992 | WIPO . |
| WO92/21313 | 12/1992 | WIPO . |
| WO94/07858 | 4/1994 | WIPO . |
| WO96/40140 | 12/1996 | WIPO . |
| WO96/40633 | 12/1996 | WIPO . |
| WO96/41609 | 12/1996 | WIPO . |
| WO97/16190 | 5/1997 | WIPO . |
| WO97/36869 | 10/1997 | WIPO . |
| WO98/13343 | 4/1998 | WIPO . |
| WO98/13355 | 4/1998 | WIPO . |

OTHER PUBLICATIONS

A. Ruhlmann, et al, Immunobiol., 198, pp. 192–206, 1997.
S. L. Schreiber, et al, Tetrahedron, 48(13), pp. 2545–2558, 1992.
D. S. Yamashita, et al, Bioorg. Med. Chem. Lett., 4(2), pp. 325–328, 1994.
D. M. Armistead, et al, Acta Cryst, D51, pp. 522–528, 1995.
W. E. Lyons, et al, Proc. Natl. Acad. Sci. USA, 91, pp. 3191–3195, 1994.
B. G. Gold, et al, J. of Neurosciecne, 15(11), pp. 7509–7516, 1996.
G. S. Hamilton, et al, Curr. Pharm. Design, 3, pp. 405–428, 1997.
B. G. Gold, et al, Exp. Neurol., 147, pp. 269–278, 1997.
S. H. Snyder, et al, Nature Med., 1(1), pp. 32–37, 1995.
B. G. Gold, et al, Neurosci. Lett., 241, pp. 25–28, 1998.
M. Bodanszky and A. Bodanszky, The Practice of Peptide Synthesis, Springer–Verlag, Berlin, 1984 (Table of Contents only).
J. L. Kofron, et al, Biochemistry, 30, pp. 6127–6134, 1991.
U. A. Germann, et al, Anticancer drugs, 8, pp. 125–140, 1997.
J. R. Hauske, et al, Bioorg. Med. Chem. Lett., 4(17), pp. 2097–2102, 1994.
M. M. Endrich, et al, Eur. J. Biochem., 252, pp. 441–446, 1998.
A. Karpas, et al, Proc. Natl. Acad. Sci. USA, 89, pp. 8351–8355, 1992.

*Primary Examiner*—Joseph McKane
*Assistant Examiner*—Sonya N Wright
*Attorney, Agent, or Firm*—Samuel J. DuBoff

[57] ABSTRACT

The present invention relates to the design, synthesis, and the peptidyl-prolyl isomerase (PPIase or rotamase) inhibitory activity of novel α,α-difluoroacetamido compounds that are neurotrophic agents (i.e. compounds capable of stimulating growth or proliferation of nervous tissue) and that bind to immunophilins such as FKBP12 and inhibit their rotamase activity. This invention also relates to pharmaceutical compositions comprising these compounds.

11 Claims, No Drawings

NEUROTROPHIC DIFLUOROAMIDE AGENTS

This application is based on provisional application No. 60/087,642 filed Jun. 2, 1998.

BACKGROUND OF THE INVENTION

Immunophilins are cytosolic proteins endowed with peptidylprolyl-cis-trans isomerase (PPIase or rotamase) activity. This family of proteins behave as chaperone molecules causing cis-trans isomerization of specific prolyl amide bonds that could be a rate limiting step in the correct folding of certain proteins. They are also involved in many cellular signal transduction pathways as partners in multi-protein complexes for which binding in the rotamase active site, but not rotamase activity per se, appears to be important (Rühlmann, et al., *Immunobiol.*, 198, pp. 192–206 (1998)). Immunosuppressive drugs such as FK506, rapamycin and cyclosporin A bind to specific groups of immunophilins. FK506 and rapamycin bind to the so-called FK506-binding proteins (e.g. FKBP-12, -25, -52), whereas the cyclophilins bind to cyclosporin A. It has been shown that binding to the 12kD immunophilin FKBP12 is necessary for FK506 to elicit its immunosuppressive activity. Subsequently, it was also found that FK506 has two binding domains: one that binds to FKBP12 and the other (the effector domain) for the complex of FK506 and FKBP12 that binds to the serine/threonine phosphatase, calcineurin. This complexation inhibits calcineurin and prevents the proliferation of T-lymphocytes, causing immunosuppression. Rapamycin has an effector domain of a different structure, and its complex with FKBP12 binds to a different target protein that, however, has the same effect of inhibiting T-lymphocyte proliferation. For a review, see S. L. Schreiber, et al., *Tetrahedron*, 48, pp. 2545–2558 (1992).

While FK506 exhibits immunosuppressive effects, analogs lacking the calcineurin binding effector domain are devoid of immunosuppressive activity. Many small molecules that contain the essential elements of the FKBP12 binding domain of FK506 but lack the calcineurin binding domain were found to retain high affinity binding to FKBP12, and behave as rotamase inhibitors (D. S. Yamshita, et al., *Bioorg. Med. Chem. Lett.*, 4, pp. 325–328 (1994); D. M. Armistead, et al., *Acta Cryst. D*, 51, pp. 522–528 (1995)).

FK506 has been shown to possess neurotrophic properties in vitro and in vivo (W. E. Lyons, et al., *Proc. Natl. Acad. Sci USA*, 91, pp. 3191–3195 (1994); B. G. Gold, et al., *J. Neurosci.*, 15, pp. 7509–7516 (1995)). However, its immunosuppressive properties as well as other serious side effects are drawbacks to its use as a neuroregenerative agent. Recently, in vitro studies in PC12 cells, SY5Y cells, and chick sensory dorsal root ganglion explant cultures have shown that small molecule, nonimmunosuppressive FKBP12 rotamase inhibitors also promote neurite outgrowth, and a number of these compounds have shown utility in reversal of CNS lesioning and nerve crush in animal models (G. S. Hamilton, et al., *Curr. Pharm. Design*, 3, pp. 405–428 (1997); B. G. Gold, et al., *Exp. Neurol.*, 147, pp. 269–278 (1997)). Thus, while the calceineurin binding domain of FK506 is necessary for immunosuppressive activity, it is not required for neurotrophic activity.

A 10–50 fold elevated expression of immunophilins in the central nervous system in comparison with the immune system is well documented (S. H. Snyder, et al., *Nature Med.*, 1, pp. 32–37 (1995)). Recently, augmented expression of FKBP12 m-RNA following facial nerve crush and sciatic nerve lesions was established in facial and lumbar motor neurons. The observed augmentation paralleled the enhanced expression of growth associated protein GAP43 mRNA (B. G. Gold, et al., *Neurosci. Lett.*, 241, pp. 25–28 (1998)). These observations make FKBP12 an attractive target for developing nonimmunosuppressive rotamase inhibitors which promote neurite outgrowth. Such compounds are potential therapeutics to reverse neuronal damage caused by neurodegenerative disease or physical trauma.

There have been disclosures of related compounds for overcoming multidrug resistance (MDR) or as immunosuppressants such as:

WO 94/07858 published Apr. 14, 1994

WO 92/19593 published Nov. 12, 1992

U.S. Pat. No. 5,622,970 granted Apr. 22, 1997

U.S. Pat. No. 5,330,993 granted Jul. 19, 1994

U.S. Pat. No. 5,192,773 granted Mar. 9, 1993

U.S. Pat. No. 5,516,797 granted May 14, 1996

WO 92/21313 published Dec. 10, 1992

European Application 564924 published Oct. 13, 1993

European Application 405994 published Jan. 2, 1991

Other prior art disclosing related compounds having neurotrophic activity are:

WO 96/40140 published Dec. 19, 1996

WO 96/40633 published Dec. 19, 1996

WO 97/16190 published May 9, 1997

WO 96/41609 published Dec. 27, 1997

U.S. Pat. No. 5,696,135 granted Dec. 9, 1997

WO 97/36869 published Oct. 9, 1997

U.S. Pat. No. 5,721,256 granted Feb. 24, 1998

U.S. Pat. No. 5,654,332 granted Aug. 5, 1997

WO 98/13343 published Apr. 2, 1998

WO 98/13355 published Apr. 2, 1998

Since there are relatively few FKBP12-binding compounds that are known to stimulate neurite growth, there remains a great need for additional neurotrophic, FKBP12-binding compounds.

SUMMARY AND OF THE INVENTION

Surprisingly, applicant has solved the aforementioned problem. The present invention relates to novel α,α-difluoro substituted acetamide compounds and pharmaceutical compositions thereof that possess neurotrophic properties.

DETAILED DESCRIPTION OF THE INVENTION

According to one embodiment, the present invention provides:

A compound with affinity for an FK506 binding protein having the formula (I):

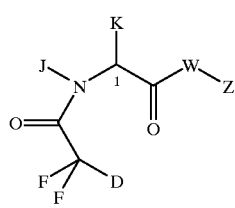

(I)

and pharmaceutically acceptable salts thereof:
wherein W is $CH_2$, O, NH, or N—($C_1$–$C_4$)-alkyl;
wherein J is hydrogen, ($C_1$–$C_4$)-alkyl or benzyl;
wherein K is ($C_1$–$C_4$)-straight or branched alkyl, benzyl or cyclohexylmethyl, or wherein J and K may be taken together to form a 5–7 membered heterocyclic ring which may contain a heteroatom selected from the group consisting of O, S, SO, and $SO_2$;
wherein the stereochemistry at carbon position 1 is R or S;
wherein Z is Q or —$(CH_2)_m$—C(H)Q'A;
wherein m is 0–3;
wherein Q is hydrogen, CHL-Ar, ($C_1$–$C_6$)-straight or branched alkyl, ($C_2$–$C_6$)-straight or branched alkenyl, ($C_5$–$C_7$)-cycloalkyl, ($C_5$–$C_7$)-cycloalkenyl, Ar substituted ($C_1$–$C_6$)-alkyl, ($C_2$–$C_6$)-alkenyl or

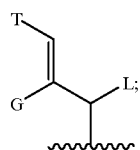

wherein L and G are independently hydrogen, ($C_1$–$C_6$)-straight or branched alkyl, ($C_2$–$C_6$)-straight or branched alkenyl;
wherein T is Ar or substituted cyclohexyl with substituents at positions 3 and 4 which are independently selected from the group consisting of hydrogen, hydroxyl, O—($C_1$–$C_4$)-alkyl or O—($C_2$–$C_4$)-alkenyl and carbonyl;
wherein D is ($C_1$–$C_6$)-straight or branched alkyl, ($C_2$–$C_6$)-straight or branched alkenyl, ($C_5$–$C_7$)-cycloalkyl or ($C_5$–$C_7$)-cycloalkenyl substituted with ($C_1$–$C_4$)-straight or branched alkyl or ($C_2$–$C_4$)-straight or branched alkenyl, O—($C_1$–$C_4$)-straight or branched alkyl, O—($C_2$–$C_4$)-straight or branched alkenyl, 2-indolyl, 3-indolyl, [($C_1$–$C_4$)-alkyl or ($C_2$–$C_4$)-alkenyl]-Ar or Ar;
wherein Ar is a carbocyclic aromatic group selected from the group consisiting of phenyl, 1-naphthyl, 2-naphthyl, indenyl, azulenyl, fluorenyl, and anthracenyl; or a heterocyclic aromatic group selected from the group consisting of 2-furyl, 3-furyl, 2-thienyl, 3-thienyl, 2-pyridyl, 3-pyridyl, 4-pyridyl, pyrrolyl, oxazolyl, thiazolyl, imidazolyl, pyrazolyl, isoxazolyl, isothiazolyl, 1,2,3-oxadiazolyl, 1,2,3-triazolyl, 1,3,4-thiadiazolyl, pyridazinyl, pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl;
wherein Ar may contain one to three substituents which are independently selected from the group consisting of hydrogen, halogen, hydroxyl, hydroxymethyl, nitro, trifluoromethyl, trifluoromethoxy, ($C_1$–$C_6$)-straight or branched alkyl, ($C_2$–$C_6$)-straight or branched alkenyl, O—[($C_1$–$C_4$)-straight or branched alkyl], O-benzyl, O-phenyl, 1,2-methylenedioxy, amino, carboxyl, N-[($C_1$–$C_5$)-straight or branched alkyl or ($C_2$–$C_5$)-straight or branched alkenyl] carboxamides, N,N-di-[($C_1$–$C_5$)-straight or branched alkyl or ($C_2$–$C_5$)-straight or branched alkenyl] carboxamides, N-morpholinecarboxamide, N-benzylcarboxamide, N-thiomorpholinocarboxamide, N-picolinoylcarboxamide, O—X, $CH_2$-$(CH_2)_p$—X, O—$(CH_2)_p$—X, $(CH_2)_p$—O—X, and CH═CH—X;
wherein X is 4-methoxyphenyl, 2-pyridyl, 3-pyridyl, 4-pyridyl, pyrazyl, quinolyl, 3,5-dimethylisoxazoyl, isoxazoyl, 2-methylthiazoyl, thiazoyl, 2-thienyl, 3-thienyl, or pyrimidyl; wherein p is 0–2;
wherein Q' and A are independently hydrogen, Ar, ($C_1$–$C_{10}$)-straight or branched alkyl, ($C_2$–$C_{10}$)-straight or branched alkenyl or alkynyl, ($C_5$–$C_7$)cycloalkyl substituted-straight ($C_1$–$C_6$)-straight or branched alkyl, ($C_2$–$C_6$)-straight or branched alkenyl or alkynyl, ($C_5$–$C_7$)-cycloalkenyl substituted ($C_1$–$C_6$)-straight or branched alkyl, ($C_2$–$C_6$)-straight or branched alkenyl or alkynyl, or Ar substituted ($C_1$–$C_6$)-straight or branched alkyl, ($C_2$–$C_6$)-straight or branched alkenyl or alkynyl wherein, in each case, any one of the $CH_2$ groups of said alkyl, alkenyl or alkynyl chains may be optionally replaced by a heteroatom selected from the group consisting of O, S, SO, $SO_2$ and NR, wherein R is selected from the group consisting of hydrogen, ($C_1$–$C_4$)-straight or branched alkyl, ($C_2$–$C_4$)-straight or branched alkenyl or alkynyl, and ($C_1$–$C_4$)-bridging alkyl wherein a bridge is formed between the nitrogen and a carbon atom of said heteroatom-containing chain to form a ring, and wherein said ring is optionally fused to an Ar group; or

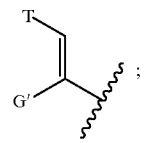

wherein G' is hydrogen, ($C_1$–$C_6$)-straight or branched alkyl or ($C_2$–$C_6$)-straight or branched alkenyl or alkynyl.

Another embodiment of this invention are compounds of formula I wherein Z is —$(CH_2)_m$—C(H)Q'A.

A preferred embodiment are compounds of formula I wherein J and K are taken together to form a piperidine ring; the stereochemistry at carbon 1 is S; W is oxygen; m is 0; D is 3,4,5-trimethoxyphenyl; Q' is 3-phenylpropyl; and A is 3-(3-pyridyl)propyl.

Another preferred embodiment are compounds of formula I wherein J and K are taken together to form a pyrrolidine ring; the stereochemistry at carbon 1 is S; W is oxygen; m is 0; D is 3,4,5-trimethoxyphenyl; Q' is 3-phenylpropyl; and A is 3-(3-pyridyl)propyl.

Another preferred embodiment are compounds of formula I wherein J and K are taken together to form a piperidine ring; the stereochemistry at carbon 1 is S; W is oxygen; m is 0; D is 3,4,5-trimethoxyphenyl; Q' is phenyl; and A is 2-phenylethyl.

Another preferred embodiment are compounds of formula I wherein J and K are taken together to form a pyrrolidine ring; the stereochemistry at carbon 1 is S; W is oxygen; m is 0; D is 3,4,5-trimethoxyphenyl; Q' is phenyl; and A is 2-phenylethyl.

Another preferred embodiment are compounds of formula I wherein J and K are taken together to form a piperidine ring; the stereochemistry at carbon 1 is S; W is oxygen; m is 0; D is 3,4,5-trimethoxyphenyl; and Q' and A are both $(C_1-C_4)$-straight chain alkyls substituted at the terminal end with a $(C_5-C_7)$-cycloalkyl, $(C_5-C_7)$-cycloalkenyl or Ar.

Another preferred embodiment are compounds of formula I wherein J and K are taken together to form a pyrrolidine ring; the stereochemistry at carbon 1 is S; W is oxygen; m is 0; D is 3,4,5-trimethoxyphenyl; and Q' and A are both $(C_1-C_4)$-straight chain alkyls substituted at the terminal end with a $(C_5-C_7)$-cycloalkyl, $(C_5-C_7)$-cycloalkenyl or Ar.

Another preferred embodiment are compounds of formula I wherein J and K are taken together to form a piperidine ring; the stereochemistry at carbon 1 is S; W is oxygen; m is 0; D is 3,4,5-trimethoxyphenyl; Q' is a $(C_5-C_7)$-cycloalkyl, $(C_5-C_7)$-cycloalkenyl or Ar; and A is a $(C_1-C_4)$-straight chain alkyl substituted at the terminal end with a $(C_5-C_7)$-cycloalkyl, $(C_5-C_7)$-cycloalkenyl or Ar.

Another preferred embodiment are compounds of formula I wherein J and K are taken together to form a pyrrolidine ring; the stereochemistry at carbon 1 is S; W is oxygen; m is 0; D is 3,4,5-trimethoxyphenyl; Q' is a $(C_5-C_7)$-cycloalkyl, $(C_5-C_7)$-cycloalkenyl or Ar; and A is a $(C_1-C_4)$-straight chain alkyl substituted at the terminal end with a $(C_5-C_7)$-cycloalkyl, $(C_5-C_7)$-cycloalkenyl or Ar.

Another aspect of the present invention provides for a pharmaceutical composition which comprises as an active ingredient an amount of a compound of formula I, or a pharmaceutically acceptable salt thereof, effective for stimulating neurite growth in nerve cells, and one or more pharmaceutically acceptable carriers, excipients or diluents thereof.

Another aspect of the present invention provides for a method for stimulating neurite growth in nerve cells comprising the step of contacting said nerve cells with a composition comprising a neurotrophic amount of a compound of formula I with affinity for an FK-506 binding protein.

Another aspect of the present invention provides for a method for stimulating neurite growth in nerve cells comprising the step of contacting said nerve cells with a composition comprising a neurotrophic amount of a compound of formula I with affinity for FKBP12.

GENERAL SUMMARY OF COMPOUND PREPARATION

The syntheses of the examples described in Table 1 was carried out using one of the methods described below that are commonly employed in peptide chemistry (see M. Bodanszky and A. Bodanszky, "The Practice of Peptide Synthesis," Springer-Verlag, Berlin (1984)):

A) An acylation reaction involving p-methylthiophenolic ester of α,α-difluoro-3,4,5-trimethoxyphenylacetic acid with appropriate prolyl or pipecolate ester in dimethylformamide (DMF) in the presence of diisopropylethylamine.

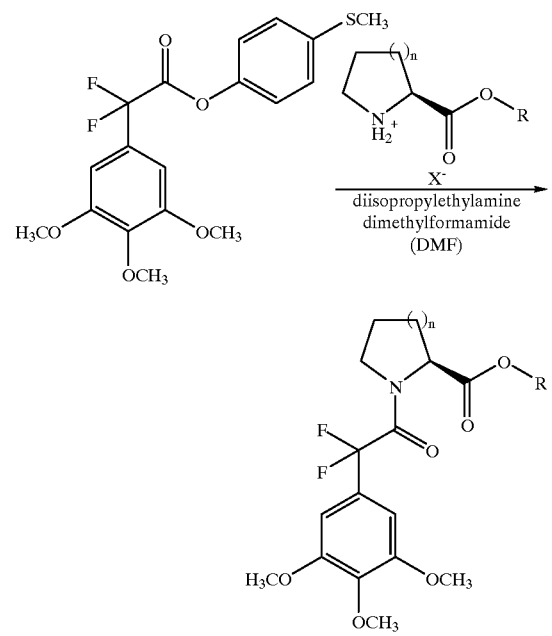

B) Acylation of proline or pipecolic acid with the p-methylthiophenolic ester of α,α-difluoro-3,4,5-trimethoxyphenylacetic acid, followed by esterification of the resulting acid with the appropriate alcohol using a water soluble carbodiimide coupling reagent in acetonitrile.

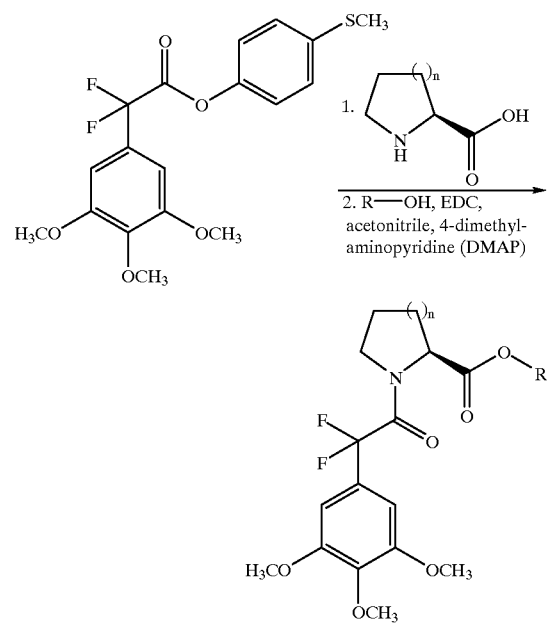

C) Schotten-Baumann reaction of in situ generated α,α-difluoro-3,4,5-trimethoxyphenylacetyl chloride with the appropriate prolyl or pipecolate ester.

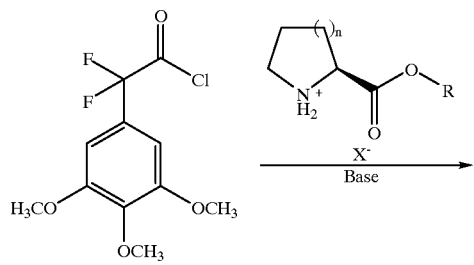
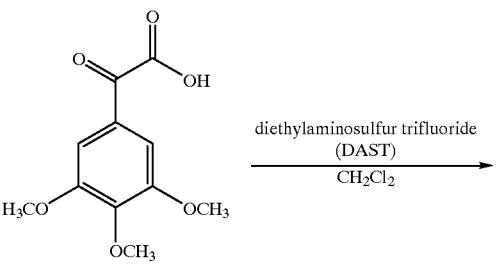

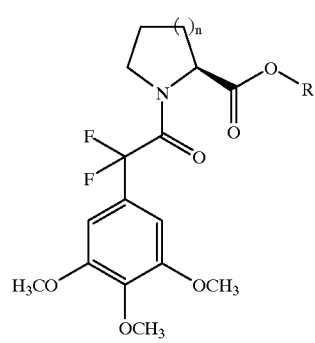
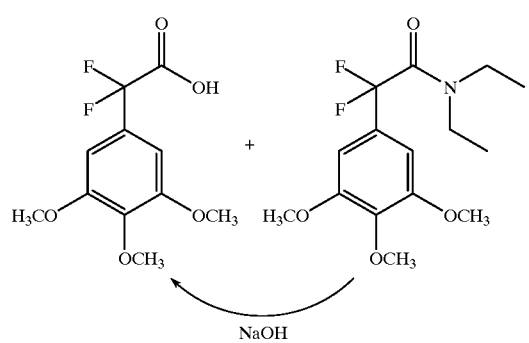

D) Peptide coupling using carbodiimide or a mixed anhydride approach were also used in some cases.

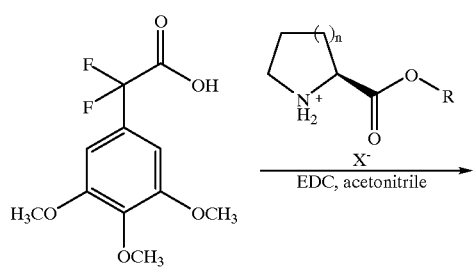
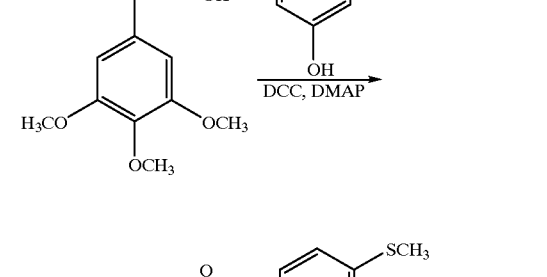

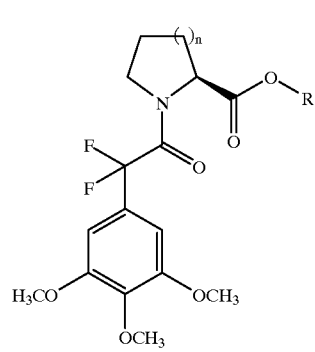
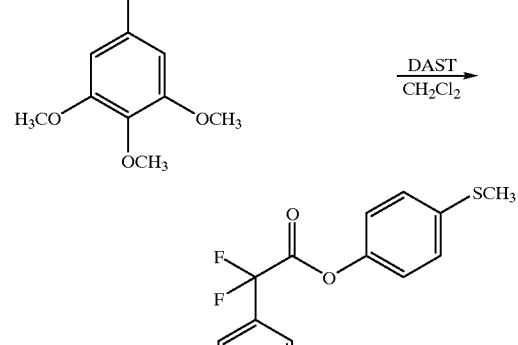

The α,α-difluoro-3,4,5-trimethoxyphenylacetic acid or its p-methylthiophenolic ester required for the above three approaches were synthesized by fluorination of the parent keto compound with diethylaminosulfurtrifluoride. In the case of the fluorination of 3,4,5-trimethoxyphenyl-α-oxoacetic acid, the corresponding N,N-diethylamide was also obtained. This N,N-diethylamide could be easily converted to the desired acid by alkaline hydrolysis.

The α,α-difluoro-3,4,5-trimethoxyphenylacetic acid was converted to the corresponding acid chloride using oxalyl chloride and catalytic dimethylformamide in methylene chloride.

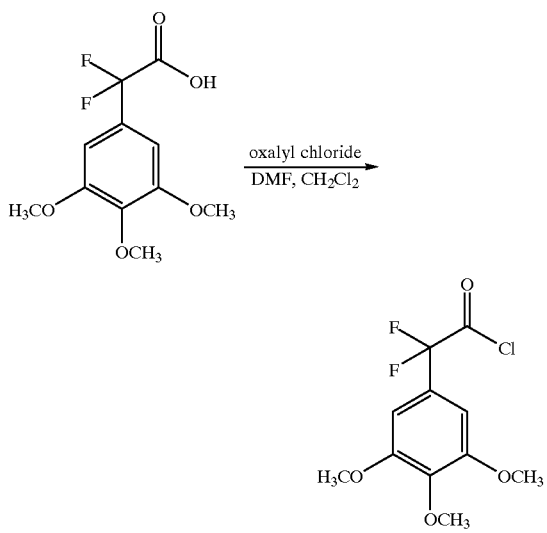

PREPARATION OF REAGENTS

General $^1$H NMR spectra in deuterated chloroform were run on a Bruker AC-300 or a Varian Gemini 300 spectrometer and chemical shifts were reported in ppm (δ) with reference to tetramethylsilane. All evaporations were carried out on a rotary evaporator under reduced pressure. Magnesium sulfate was used for drying the organic layer after extractive work up. LC-MS analysis were carried out on a Shimadzu instrument using either of the following two systems: System 1 consists of a PHX-LUNA C18 column (4.6×30 mm) employing a 4 min linear gradient of 20% to 100% solvent B:A (solvent A: 10% methanol, 90% water, 0.1% trifluoroacetic acid; solvent B: 90% methanol, 10% water, 0.1% trifluoroacetic acid) with the UV detector set at 220 nm. System 2 consists of a YMC C18 column (4.6×50 mm) employing a 4 or 8 min linear gradient of 0% to 100% solvent B:A with other conditions as described above for system 1. The water soluble carbodiimides used were either the hydrochloride salt or the methiodide of 1-(3-dimethylaminopropyl)-3-ethylcarbodiimide (EDC). Abbreviations used were in accordance with the guidelines provided by the American Chemical Society for their publications.

p-(Methylthio)phenolic ester of 3,4,5-trimethoxyphenyl-α-oxoacetic acid

To a stirred solution of 3,4,5-trimethoxyphenyl-α-oxoacetic acid (12.0 g, 49.9 mmol) in anhydrous acetonitrile (150 mL) at ambient temperature was added 4-(methylthio)-phenol (8.40 g, 59.9 mmol), dicyclohexylcarbodiimide (DCC) (15.4 g, 74.9 mmol) and 4-dimethylaminopyridine (0.428 g, 3.50 mmol) under nitrogen. The reaction mixture was stirred for 8 h, then cooled to 0° C. in an ice bath and 1M solution of oxalic acid in acetonitrile was added. The precipitated dicyclohexylurea was removed by filtration. The filtrate was diluted with ethyl acetate (400 mL) and the organic layer was washed with water (3×200 mL), brine (200 mL) and dried. The solvent was evaporated to give a pale yellow solid which was recrystallized from 2-propanol to give the pure ester (11.0 g, 61% yield). MS: M+H =363. $^1$H-NMR: 7.41 (s, 2H), 7.35 (d, J =8.7 Hz, H$_2$ & H$_6$, 2H), 7.21 (d, J=8.7 Hz, H$_3$ & H$_5$, 2H), 3.99 (s, 3H), 3.94 (s, 6H), 2.52 (s, 3H).

p-(Methylthio)phenolic ester of α,α-difluoro-3,4,5-trimethoxyphenylacetic acid To a stirred solution of the p-(methylthio)phenolic ester of 3,4,5-trimethoxyphenyl-α-oxoacetic acid (1.00 g, 2.76 mmol) in anhydrous methylene chloride (10 mL) at room temperature was added diethylaminosulfurtrifluoride (DAST) (4.44 g, 27.6 mmol) under nitrogen. The reaction mixture was stirred overnight. It was then cooled in an ice bath and excess DAST was quenched by dropwise addition of water. Ethyl acetate (150 mL) was then added and the organic layer was washed repeatedly with water until the pH of the aqueous layer was neutral. The organic layer was then washed with brine (50 mL), dried, and the solvent evaporated to afford the title compound (0.961 g, 2.50 mmol, 91%) as a brown solid. $^1$H-NMR: 7.27 (d, J=8.7 Hz, H$_2$ & H$_6$, 2H), 7.04 (d, J=8.8 Hz, H$_3$ & H$_5$, 2H), 6.92 (s, 2H), 3.92 (s, 6H), 3.91 (s, 3H), 2.48 (s, 3H).

α,α-Difluoro-3,4,5-trimethoxyphenylacetic acid

To a stirred solution of 3,4,5-trimethoxyphenyl-α-oxoacetic acid (3.81 g, 15.8 mmol) in anhydrous methylene chloride (30 mL) at room temperature was added DAST (20.4 g, 127 mmol) under nitrogen and the mixture was stirred overnight. The mixture was then cooled in an ice bath and excess DAST was quenched by dropwise addition of water. Ethyl acetate (300 mL) was added and the organic layer was washed with saturated aqueous sodium bicarbonate (2×100 mL) followed by water (100 mL). The residue obtained after drying and evaporation was purified by silica gel chromatography, eluting with hexane/ethyl acetate (9:1 to 7:3), to give the N,N-diethylamide derivative (2.10 g, 6.62 mmol, 42%) as a pale yellow solid. $^1$H-NMR: 6.77 (s, 2H), 3.88 (s, 9H), 3.45 (q, J=7.0 Hz, 2H), 3.25 (q, J=7.0 Hz, 2H), 1.20 (t, J=7.0 Hz, 3H), 1.10 (t, J=6.9 Hz, 3H). Bicarbonate washing after acidification and extractive work up with ethylacetate gave the crude title compound. Purification by reversed phase column (C18) chromatograhy eluting with water/methanol/trifluoroacetic acid (69.9:30:0.1) gave the pure difluoro acid (0.616 g, 2.34 mmol, 15%) as a white solid. $^1$H-NMR: 6.85 (s, 2H), 3.90 (s, 6H), 3.89 (s, 3H). Anal. C: 50.59, H: 4.72, F: 14.24 (found), C: 50.39, H: 4.61, F: 14.49 (calcd). The N,N-diethylamide (2.00 g, 6.30 mmol) obtained above was hydrolyzed to the title acid by heating a solution in ethanol (5 mL) with 10% sodium hydroxide (13 mL) at reflux for 4 h. Acidification followed by extractive work up with ethyl acetate gave the crude acid which was purified as described above to give 1.51 g of the title compound as a white solid.

α,α-Difluoro-3,4,5-trimethoxyphenylacetylchloride

A stirred solution of α,α-difluoro-3,4,5-trimethoxyphenylacetic acid (1.50 g, 6.63 mmol) in anhydrous methylene chloride (20 mL) was treated with oxalyl chloride (2.52 g, 19.8 mmol) and 1 drop of dimethylformamide. After vigorous effervescence ceased, the reaction mixture was stirred for 3 h. The solvents were evaporated and traces of oxalyl chloride were removed by repeated evaporation with anhydrous methylene chloride to give the acid chloride (1.61 g, 99% yield) as a dark yellow solid.

EXAMPLE 1

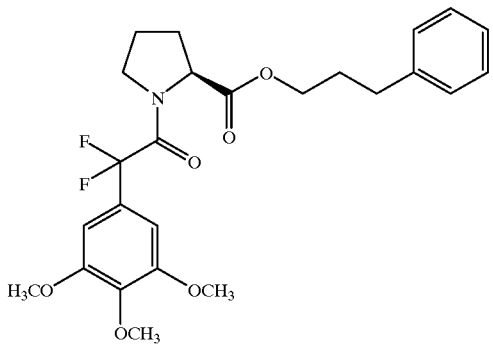

A suspension of N-Boc-L-proline (6.04 g, 28.0 mmol), 3-phenylpropanol (4.58 g, 33.6 mmol), DCC (8.68 g, 42.0 mmol), and 4-dimethylaminopyridine (0.210 g, 1.72 mmol) in anhydrous ether (60 mL) was stirred under nitrogen for 8 h. Water (200 mL) was added and the mixture was extracted with ethyl acetate (3×200 mL). The organic layer was separated and washed with water (2×100 mL), brine (2×100 mL), dried and evaporated. Purification of the residue by silica gel chromatography eluting with hexane/ethyl acetate (7:3 to 7:3) gave the pure phenylpropyl ester (7.62 g, 81%) as a colorless oil. MS: M+H=334. $^1$H NMR: 7.26 (m, 2H), 7.17 (m, 3H), 4.31 & 4.21 (dd, J=8.1, 3.2 Hz, 1H), 4.09 (m, 2H), 3.59–3.32 (m, 2H), 2.64 (t, J=8.9 Hz, 2H), 2.19 (m, 1H), 1.91 (m, 5H), 1.42 (s, 4H), 1.39 (s, 6H). A portion of this material (0.393 g, 1.18 mmol), in methylene chloride (8 mL) was treated with trifluoroacetic acid (0.13 mL). After 1 h volatiles were evaporated and a solution of the resulting trifluoroacetate salt in dimethylformamide (12 mL) was combined with p-methylthiophenolate ester of 3,4,5-trimethoxy-α,α-difluorophenyl acetic acid (0.428 g, 1.18 mmol) and diisopropylethylamine (0.152 g, 1.18 mmol). The solution was stirred for 18 h, and then diluted with ethyl acetate (100 mL), washed with water (50 mL), and dried. The solvent was removed by evaporation. The residue was purified by silica gel chromatography, eluting with hexane/ethyl acetate (9:1 to 4:1) to give the product (0.360 g, 0.755 mmol, 64%) as a brown oil. (M+H)=478. $^1$H NMR: 7.25 (m, 2H), 7.17 (m, 3H), 6.87 (s, 2H), 4.57 (m, 1H), 4.10 (m, 2H), 3.87 (s, 6H), 3.85 (s, 3H), 3.57 (m, 2H), 2.68 (t, J=7.5 Hz, 2H), 2.16 (m, 1H), 1.96 (m, 5H).

EXAMPLE 2

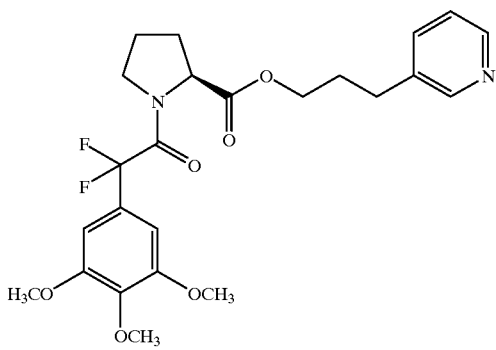

Esterification of N-Boc-L-proline (1.01 g, 4.60 mmol) with 3-(3'-pyridyl)propan-1-ol (0.772 g, 5.60 mmol) was carried out using DCC (1.45 g, 7.00 mmol) and 4-dimethylaminopyridine (0.102 g, 0.834 mmol) in anhydrous ether (25 mL). Work up was carried out as described above for example 1. Purification by silica gel chromatography, eluting with hexane/ethyl acetate (7:3 to 3:7) gave the N-Boc-prolylester of 3-(3'-pyridyl)propan-1-ol (1.34 g, 4.00 mmol, 87%) as a colorless oil. MS: M+H=335. $^1$H-NMR: 8.42 (m, 2H), 7.50 (m, 1H), 7.20 (m, 1H), 4.36 & 4.22 (dd, J=8.0, 3.0 Hz, 1H, rotamers), 4.17 (m, 2H), 3.49 (m, 2H), 2.70 (t, J=10.0 Hz, 2H), 2.20 (m, 1H), 1.91 (m, 5H), 1.43 (s, 4.5H), 1.39 (s, 4.5H). The N-Boc-prolylester of 3-(3'-pyridyl)propan-1-ol (0.271 g, 0.811 mmol), was deprotected and coupled with the p-methylthiophenolate ester of 3,4,5-trimethoxy-α,α-difluorophenyl acetic acid (0.312 g, 0.811 mmol), diisopropylethylamine (0.104 g, 0.811 mmol) in dimethylformamide (20 mL) as described in example 1. The crude product was partitioned between ethyl acetate (200 mL) and 1M hydrochloric acid (2×25 mL). The aqueous layer was basified with sodium bicarbonate and extracted with ethyl acetate (3×100 mL). The solution was evaporated after washing with water and drying. Purification of the residue by silica gel chromatography, eluting with chloroform/methanol (99.3:0.7) provided the title compound (0.331 g, 0.692 mmol, 85%) as pale brown oil. M+H=479. $^1$H-NMR: 8.38 (m, 2H), 7.45 (m, 1H), 7.18 (m, 1H), 6.83 (s, 2H), 4.57 & 4.53 (dd, J=8.5, 3.2 Hz, 1H, rotamers), 4.17 (m, 1H), 4.06 (m, 1H), 3.83 (s, 6H), 3.81 (s, 3H), 3.53 (m, 2H), 2.66 (t, J=7.6 Hz, 2H), 2.12 (m, 1H), 1.88 (m, 5H).

EXAMPLE 3

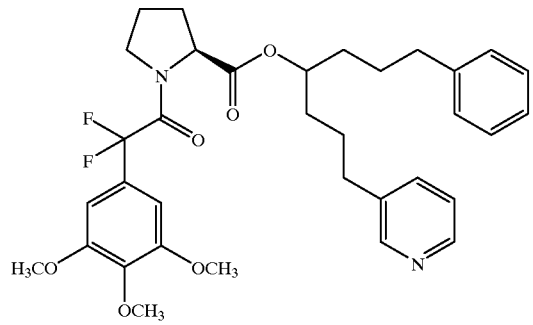

The coupling of L-proline with the p-(methylthio) phenolic ester of (α,α-difluoro-3,4,5-trimethoxyphenylacetic acid was carried out as described above for example 2. The trimethoxydifluorophenylac-etamidoproline derivative was obtained in 89% yield after purification by silica gel chromatography, eluting with methylene chloride/ethyl acetate/acetic acid (70:27.5:2.5). M+H= 360. $^1$H-NMR: 8.51 (br, OH), 6.88 (s, 2H), 4.65 (m, 1H), 3.89 (s, 9H), 3.55 (m, 2H), 2.20 (m, 2H), 1.98 (m, 2H). LC-MS: System 1, $t_R$=5.2 min. Water soluble carbodiimide (EDC hydrochloride, 0.318 g, 1.66 mmol) mediated esterification of the intermediate acid (0.400 g, 1.11 mmol) with 1-phenyl-7-(3'-pyridyl)-heptan-4-ol (0.358 g, 1.33 mmol), in the presence of a catalytic amount of dimethylaminopyridine (0.101 g, 0.830 mmol) in acetonitrile (25 mL) gave, after extractive work up with ethyl acetate and water, the crude product. Purification by silica gel chromatography gave the title compound (0.425 g, 0.695 mmol, 63%) as a yellow oil. MS: M+H=611. $^1$H-NMR: 8.36 (m, 2H), 7.58–7.39 (m, 1H), 7.22–7.07 (m, 6H), 6.80 (d, J=3.1 Hz, 2H), 4.88 (m, 1H), 4.48 (m, 1H), 3.79 (m, 9H), 3.44 (m, 2H), 2.54 (m, 4H), 2.08 (m, 1H), 1.83 (m, 2H), 1.52 (m, 9H).

LC-MS: System 2 (8 min gradient), $t_R$ for the diastereomers was 6.9 and 7.2 min.

EXAMPLE 4

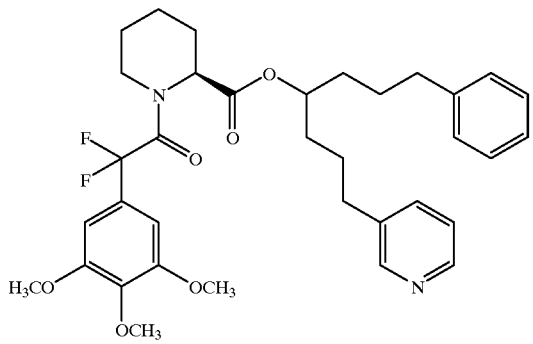

N-Boc-L-pipecolic acid (0.280 g, 1.22 mmol) was esterified with 1-phenyl-7-(3'-pyridyl)-heptan-4-ol (0.394 g, 1.46 mmol) employing EDC hydrochloride (0.350 g, 1.83 mmol) and 4-dimethylaminopyridine (0.081 g, 0.663 mmol) in acetonitrile (25 mL). Purification by silica gel chromatography, eluting with chloroform/methanol (100:0 to 99:1), gave the pure 1-phenyl-7-(3'-pyridyl)-heptan-4-ol ester of N-Boc-pipecolic acid in 85% yield (0.498 g) as a colorless oil. MS: M+H=481. LC-MS: System 2 (4 min gradient), $t_R$=3.8 min. A portion of this N-Boc ester (0.369 g, 0.768 mmol) was deprotected as described in example 1 with trifluoroacetic acid. The crude product was then coupled with α,α-difluoro-3,4,5-trimethoxyphenylacetic acid (0.241 g, 0.921 mmol), using EDC hydrochloride (0.220 g, 1.15 mmol) and 4-dimethylaminopyridine (0.101 g, 0.826 mmol) in acetonitrile (25 mL). After extractive work up as described in example 1, the product was purified by silica gel chromatography, eluting with hexane/ethyl acetate (4:1 to 1:1), to give the title compound (0.624 g, 1.05 mmol, 78%) as a pale yellow oil. MS: M+H=625. $^1$H-NMR: 8.38–8.34 (m, 2H), 7.75–7.00 (m, 7H), 6.76–6.63 (m & s, 2H), 5.25–4.10 (4×m, 2H), 3.80–3.50 (m, 1OH), 3.00–2.85 (m, 1H), 2.52 (m, 2H), 2.25–1.00 (4×m, 16H). LC-MS: System 2 (4 min gradient), $t_R$, for the diastereomers=3.6 and 3.8 min. Anal. $C_{35}H_{42}N_2O_6F_2$, C=67.40, H=6.85, N=4.23, F=5.86 (found) C=67.29, H=6.78, N=4.48, F=6.08 (calcd.).

EXAMPLE 5

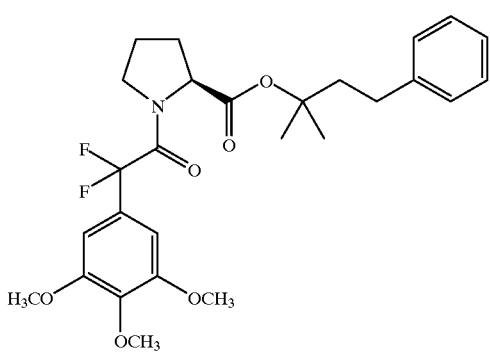

N-Boc-L-proline (2.01 g, 9.29 mmol) was esterified with 1,1-dimethyl-3-phenyl propanol (1.83 g, 11.1 mmol) using EDC methiodide (4.14 g, 13.9 mmol) and 4-dimethylaminopyridine (0.100 g, 0.815 mmol) in anhydrous acetonitrile (30 mL) as described in example 4. Following aqueous/organic extractive work up, purification by silica gel chromatography, eluting with hexane:ethyl acetate (95:5 to 80:20), gave pure 1,1-dimethyl-3-phenylpropyl ester (1.13 g, 3.13 mmol, 34%) as a colorless oil. MS: M+H=362. $^1$H-NMR: 7.29 (m, 2H), 7.18 (m, 3H), 4.23 & 4.17 (dd, J=8.9 & 3.4 Hz, 1H), 3.60–3.35 (m, 2H), 2.65 (m, 2H), 2.27–1.83 (br m, 6H), 1.46 (s, 4H), 1.44 (s, 6H). A portion of this Boc-protected ester (0.689g, 1.90 mmol) was deprotected with trifluoroacetic acid as described in example 1 and acylated with the p-(methylthio)phenolic ester of α,α-difluoro-3,4,5-trimethoxyphenylacetic acid (0.533 g, 1.39 mmol) in the presence of diisopropylethylamine (0.246 g, 1.90 mmol) in dimethylformamide (10 mL). After extractive work up using ethyl acetate, the crude product was purified by silica gel chromatography, eluting with hexane/ethyl acetate (9:1 to 7:3), to give the title compound (0.350 g, 0.693 mmol, 36%) as a pale brown oil. MS: M+H=506. $^1$H-NMR: 7.27 (m, 2H), 7.16 (m, 3H), 6.90 (s, 2H), 4.52 (m, 1H), 3.86 (s, 9H), 3.57 (m, 2H), 2.75–2.50 (m, 2H), 2.20–1.87 (m, 6H), 1.49 (d, J=2.7 Hz, 6H).

EXAMPLE 6

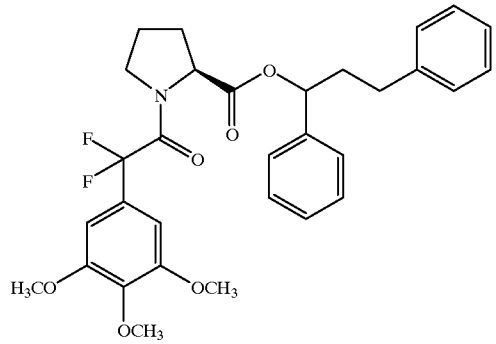

The coupling of L-proline with the p-(methylthio) phenolic ester of α,α-difluoro-3,4,5-trimethoxyphenylacetic acid was carried out as described in example 5. The intermediate trimethoxydifluorophenylacetamidoproline derivative (0.455 g, 1.26 mmol) was esterified with 1,3-diphenylpropanol (0.325 g, 1.51 mmol) using EDC hydrochloride (0.362 g, 1.90 mmol) and 4-dimethylaminopyridine (0.081g, 0.656 mmol) in anhydrous acetonitrile (20 mL). Following extractive work up, purification by silica gel chromatography, eluting with hexane/ethyl acetate (9:1 to 7:3), gave the desired compound (0.182 g, 0.328 mmol, 26%) as a colorless oil. MS: M+H= 554. $^1$H-NMR: 7.31 (m, 7H), 7.20 (m, 3H), 6.81 (s, 2H), 5.74 (m, 1H), 4.71 (m, 1H), 3.88 (d, J=7.1 Hz, 3H), 3.78 (d, J=5.5 Hz, 6H), 3.59 (m, 2H), 2.63 (m, 2H), 2.33–1.85 (m, 6H). LC-MS: System 2 (8 min gradient), $t_R$=8.2 min.

EXAMPLE 7

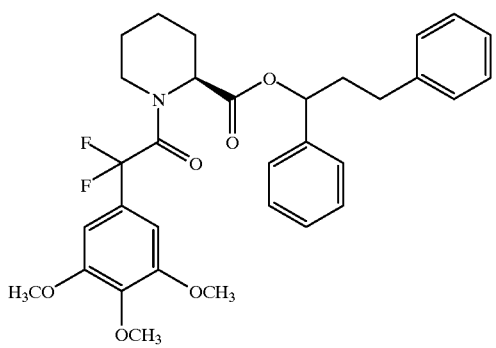

N-Boc pipecolic acid (0.345 mg, 1.5 mmol) was esterified as described in example 5 with 1,3-diphenyl-1-propanol to obtain the diphenylpropyl ester in 45% yield. MS: M+H= 424. LC-MS: System 2 (4 min gradient), $t_R$=4.8 min. A portion of this N-Boc-protected ester (270 mg, 0.64 mmol) was deprotected with trifluoroacetic acid as described in example 1. The resulting trifluoroacetate salt in dichloromethane (4 mL) was acylated with freshly prepared α,α-difluoro-3,4,5-trimethoxyphenylacetyl chloride (201 mg, 1.2 equiv). After 15 h, the solvent was evaporated and the residue was purified by chromatography on reversed phase (C18) silica gel, eluting first with methanol/0.1% trifluoroacetic acid in water (7:3). This was followed by silica gel chromatography of the combined fractions, eluting with ethyl acetate/hexane (3:7), to give a colorless oil (183 mg, 50% yield). MS: M+H=568. $^1$H-NMR: 7.38–7.15 (m, 10H), 6.85–6.70 (set of 4 s, 2H), 5.78–5.73 (m, 1H), 5.42–4.60 (2 sets of m, 1H), 4.07–3.67 (m, 10H), 2.97–2.85 (m, 1H), 2.72–2.53 (m, 2H), 2.42–2.08 (m, 3H), 1.85–1.00 (m, 5H). LC-MS: System 2 (4 min gradient), $t_R$=4.6 min. Anal. $C_{32}H_{35}NO_6F_2 \cdot 0.25$ $CH_3COOC_2H_5$, C=67.10, H=6.56, N=2.13, F=6.85 (found), C=67.22, H=6.32, N=2.38, F=6.44 (calcd.).

EXAMPLE 8

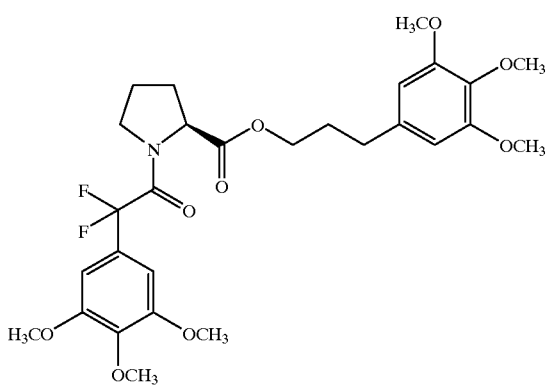

The coupling of L-proline with the p-(methylthio) phenolic ester of α,α-difluoro-3,4,5-trimethoxyphenylacetic acid was carried out as described for example 5. The intermediate timethoxyphenyldifluoroacetamidoproline derivative (0.455 g, 1.26 mmol) was esterified with 3-(3,4,5-trimethoxyphenyl)propan-1-ol as described in example 6 to give the trimethoxyphenylpropyl ester in 42% as a colorless oil. MS: M+H=568. $^1$H-NMR: 6.89 (s, 2H), 6.43 (s, 2H), 4.61 (m, 1H), 4.22 (m, 1H), 4.10 (m, 1H), 3.88 (m, 9H), 3.84 (m, 9H), 3.57 (m, 2H), 2.67 (m, 2H), 2.20 (m, 1H), 1.96 (m, 5H). LC-MS: System 2 (8 min gradient), $t_R$=7.0 min.

EXAMPLE 9

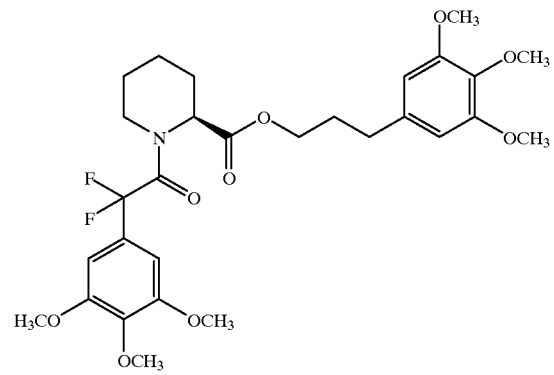

The synthesis of this compound was carried out as as described for example 7. N-Boc pipecolic acid (345 mg, 1.5 mmol) was esterified with 3-(3,4,5-trimethoxyphenyl)propan-1-ol to obtain the trimethoxyphenylpropyl ester in 52% yield. MS: M+H=438. LC-MS: System 2 (4 min gradient), $t_R$=4.2 min. A portion of this Boc-protected ester (325 mg, 0.744 mmol) was deprotected and acylated as described in example 7 with α,α-difluoro-3,4,5-trimethoxyphenylacetyl chloride to obtain 183 mg (42%) of the desired compound. MS: M+H=582. $^1$H-NMR: 6.84–6.38 (set of 4 s, 4H), 5.42–4.55 (2×m, 1H), 4.24–3.75 (m, 21H), 3.04–2.96 (m, 1H), 2.67–2.54 (m, 2H), 2.36–2.10 (m, 1H), 2.03–1.15 (m, 7H). LC-MS: System 2 (4 min gradient), $t_R$=4.0 min. Anal. $C_{29}H_{37}F_2NO_9 \cdot 0.25$ $CH_3COOC_2H_5$, C=59.66, H=6.63, N=2.24, F=6.70 (found), C=59.69, H=6.51, N=2.32, F=6.29 (calcd.).

EXAMPLE 10

FKBP12 Rotamase Inhibition Assay

The rotamase activity of FKBP-12 was measured by an adaptation of the assay described by Kofron et al. (*Biochemistry*, 30, pp. 6127–6134 (1991)). The assay was carried out at 4° C. with 1 mg chymotrypsin/mL of assay solution with succinyl-Ala-Leu-Pro-Phe-p-nitroanilide as the substrate. Chymotrypsin rapidly hydrolyzes the peptide bond on the C-terminal side of the Phe of the trans form of the peptide and releases the chromogenic p-nitroaniline. The rate of the reaction is controlled by the rate of conversion of the cis form of the peptide to the transform, the reaction catalyzed by FKBP12. The apparent $K_i$ values of compounds of formula I for inhibition of the rotamase activity were determined by measuring decreases in the first order rate constant of the reaction catalyzed by FKBP12 as a function of the concentrations of the compounds described herein. $K_i$ is the concentration of the compound that causes 50% inhibition of rotamase activity which is indicative of neurite outgrowth activity. The results are presented in Table I.

EXAMPLE 11

Assay of Neurite Outgrowth in PC12 Cell Cultures

PC-12A rat pheochromocytoma cells are maintained in Dulbecco's modified Eagle's medium (DMEM) supplemented with 10% fetal calf serum and 5% calf serum at 37° C. and 5% $CO_2$. Cells to be assayed are plated at $10^4$ per well of a 24 well plate an allowed to attach for 4–18 h.

The medium is then replaced with DMEM plus 0.1% BSA (bovine serum albumin), submaximal concentrations of NGF (nerve growth factor) (as determined by neurite outgrowth assay), and varying concentrations of the FKBP12 binding compound (0.1 nM–10 μM) in a final concentration of 0.25% DMSO (dimethylsulfoxide). Control cultures are treated with NGF in the absence of the FKBP12 binding compound. After 72 hours, cultures are fixed with 4% formalin in PBS (phosphate buffered saline), stained with Commassie Blue, and approximately 200 cells are counted in random fields of each well. Cells with neurites longer than one cell diameter are counted as a percentage of total number of cells.

The FKBP12 binding compounds of formula I utilized in this invention cause a significant increase in neurite outgrowth over control cultures.

Additionally, compounds of this invention may also show benefit as reversers of multidrug resistance (MDR) in cancer chemotherapy and as agents for the treatment of HIV infection. Nonimmunosuppressive compounds possessing the structural elements of the FKBP12 binding portion of FK506 have shown utility in reversing P-glycoprotein mediated MDR (U. A. Germann, et al., *Anti-Cancer Drugs*, 8, pp. 125–140 (1997)). In addition, there has been no direct correlation shown between rotamase inhibitory activity and MDR reversing activity (J. R. Hauske, et al., *Bioorg. Med. Chem. Lett.*, 4, pp. 2097–2102 (1994)). In the area of HIV infection, it is known that immunophilins, including the FK506 binding proteins (FKBPs), are involved in facilitating binding of the HIV envelope protein gp120 to host CD4 receptors (M. M. Endrich, et al., *Eur. J. Biochem.*, 252, pp. 441–446(1998)), and that FK506 inhibits the growth of HIV-infected cells (A. Kapas, et al., *Proc. Natl. Acad. Sci USA*, 89, pp. 8351–8355 (1992)).

TABLE 1

Rotamase inhibition data with selected examples

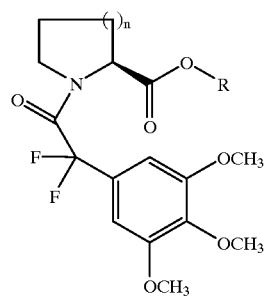

| Example | n | R | $K_i$ (nM) | Percent Inhibition at 10 μM |
|---|---|---|---|---|
| 1 | 1 | 3-phenylpropyl | 1300 | 97 |
| 2 | 1 | 3-(3-pyridyl)propyl | 877 | 97 |
| 3 | 1 | 4-[7-(3-pyridyl)-1-phenylheptyl] | 104 | 97 |
| 4 | 2 | 4-[7-(3-pyridyl)-1-phenylheptyl] | 19 | 98 |
| 5 | 1 | 3-(1-phenyl-3-methylbutyl) |  | 70 |
| 6 | 1 | 1-(1,3-diphenylpropyl) | 83 | 100 |
| 7 | 2 | 1-(1,3-diphenylpropyl) |  | 94 |
| 8 | 1 | 3-(3',4',5'-trimethoxyphenyl)propyl |  | 38 |
| 9 | 2 | 3-(3',4',5'-trimethoxyphenyl)propyl | 109 | 99 |

If pharmaceutically acceptable salts of the compounds of formula I are used, those salts are preferably derived from inorganic or organic acids and bases. Included among such acid salts are the following: acetate, aspartate, bisulfate, butyrate, citrate, fumarate, hydrochloride, hydrobromide, hydroiodide, lactate, maleate, oxalate, persulfate, propionate, succinate, tartrate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir.

It should also be understood that a specific dosage and treatment regimen for any particular patient will depend upon a variety of factors, including the activity of the specific compound employed, the age, body weight, general health, sex, diet, time of administration, rate of excretion, and the judgment of the treating physician and the severity of the particular disease being treated. The amount of compound of formula I will also depend upon the particular FKBP12 binding compound in the composition.

The amount of compound of formula I utilized in these methods is between about 0.01 and 100 mg/kg body weight/day.

What is claimed is:

1. A compound having the formula (I):

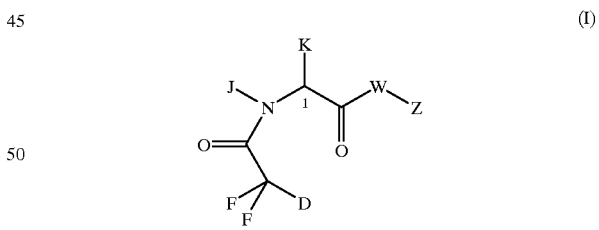

and pharmaceutically acceptable salts thereof:

wherein W is $CH_2$, O, NH, or N—$(C_1$–$C_4)$-alkyl;

wherein J is hydrogen, $(C_1$–$C_4)$-alkyl or benzyl;

wherein K is $(C_1$–$C_4)$-straight or branched alkyl, benzyl or cyclohexylmethyl, or wherein J and K may be taken together to form a 5–7 membered heterocyclic ring which may contain a heteroatom selected from the group consisting of O, S, SO, and $SO_2$;

wherein the stereochemistry at carbon position 1 is R or S;

wherein Z is Q or —$(CH_2)_m$—C(H)Q'A;

wherein m is 0–3;

wherein Q is hydrogen, CHL-Ar, ($C_1$–$C_6$)-straight or branched alkyl, ($C_2$–$C_6$)-straight or branched alkenyl, ($C_5$–$C_7$)-cycloalkyl, ($C_5$–$C_7$)-cycloalkenyl, Ar substituted ($C_1$–$C_6$)-alkyl, ($C_2$–$C_6$)-alkenyl or

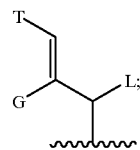

wherein L and G are independently hydrogen, ($C_1$–$C_6$)-straight or branched alkyl, ($C_2$–$C_6$)-straight or branched alkenyl;

wherein T is Ar or substituted cyclohexyl with substituents at positions 3 and 4 which are independently selected from the group consisting of hydrogen, hydroxyl, O—($C_1$–$C_4$)-alkyl or O—($C_2$–$C_4$)-alkenyl and carbonyl;

wherein D is ($C_1$–$C_6$)-straight or branched alkyl, ($C_2$–$C_6$)-straight or branched alkenyl, ($C_5$–$C_7$)-cycloalkyl or ($C_5$–$C_7$)-cycloalkenyl substituted with ($C_1$–$C_4$)-straight or branched alkyl or ($C_2$–$C_4$)-straight or branched alkenyl, O—($C_1$–$C_4$)-straight or branched alkyl, O—($C_2$–$C_4$)-straight or branched alkenyl, [($C_1$–$C_4$)-alkyl or ($C_2$–$C_4$)-alkenyl]-Ar or Ar;

wherein Ar is a carbocyclic aromatic group selected from the group consisiting of phenyl, 1-naphthyl, 2-naphthyl, indenyl, azulenyl, fluorenyl, and anthracenyl;

wherein Ar may contain one to three substituents which are independently selected from the group consisting of hydrogen, halogen, hydroxyl, hydroxymethyl, nitro, trifluoromethyl, trifluoromethoxy, ($C_1$–$C_6$)-straight or branched alkyl, ($C_2$–$C_6$)-straight or branched alkenyl, O—[($C_1$–$C_4$)-straight or branched alkyl], O-benzyl, O-phenyl, 1,2-methylenedioxy, amino, carboxyl, N-[($C_1$–$C_5$)-straight or branched alkyl or ($C_2$–$C_5$)-straight or branched alkenyl] carboxamides, N,N-di-[($C_1$–$C_5$)-straight or branched alkyl or ($C_2$–$C_5$)-straight or branched alkenyl] carboxamides, N-benzylcarboxamide, O—X, $CH_2$—$(CH_2)_p$—X, O—$(CH_2)_p$—X, $(CH_2)_p$—O—X, and CH=CH—X;

wherein X is 4-methoxyphenyl;

wherein p is 0–2;

wherein Q' and A are independently hydrogen, Ar, ($C_1$–$C_{10}$)-straight or branched alkyl, ($C_2$–$C_{10}$)-straight or branched alkenyl or alkynyl, ($C_5$–$C_7$)cycloalkyl substituted-straight ($C_1$–$C_6$)-straight or branched alkyl, ($C_2$–$C_6$)-straight or branched alkenyl or alkynyl, ($C_5$–$C_7$)-cycloalkenyl substituted ($C_1$–$C_6$)-straight or branched alkyl, ($C_2$–$C_6$)-straight or branched alkenyl or alkynyl, or Ar substituted ($C_1$–$C_6$)-straight or branched alkyl, ($C_2$–$C_6$)-straight or branched alkenyl or alkynyl wherein, in each case, any one of the $CH_2$ groups of said alkyl, alkenyl or alkynyl chains may be optionally replaced by a heteroatom selected from the group consisting of O, S, SO, $SO_2$ and NR, wherein R is selected from the group consisting of hydrogen, ($C_1$–$C_4$)-straight or branched alkyl, ($C_2$–$C_4$)-straight or branched alkenyl or alkynyl, and ($C_1$–$C_4$)-bridging alkyl wherein a bridge is formed between the nitrogen and a carbon atom of said heteroatom-containing chain to form a ring, and wherein said ring is optionally fused to an Ar group; or

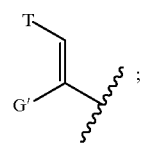

wherein G' is hydrogen, ($C_1$–$C_6$)-straight or branched alkyl or ($C_2$–$C_6$)-straight or branched alkenyl or alkynyl.

2. A compound of claim 1 wherein Z is —$(CH_2)_m$—C(H)Q'A.

3. A compound of claim 2 wherein J and K are taken together to form a piperidine ring; the stereochemistry at carbon 1 is S; W is oxygen; m is 0; D is 3,4,5-trimethoxyphenyl; Q' is phenyl; and A is 2-phenylethyl.

4. A compound of claim 2 wherein J and K are taken together to form a pyrrolidine ring; the stereochemistry at carbon 1 is S; W is oxygen; m is 0; D is 3,4,5-trimethoxyphenyl; Q' is phenyl; and A is 2-phenylethyl.

5. A compound of claim 2 wherein J and K are taken together to form a piperidine ring; the stereochemistry at carbon 1 is S; W is oxygen; m is 0; D is 3,4,5-trimethoxyphenyl; and Q' and A are both ($C_1$–$C_4$)-straight chain alkyls substituted at the terminal end with a ($C_5$–$C_7$)-cycloalkyl, ($C_5$–$C_7$)-cycloalkenyl or Ar.

6. A compound of claim 2 wherein J and K are taken together to form a pyrrolidine ring; the stereochemistry at carbon 1 is S; W is oxygen; m is 0; D is 3,4,5-trimethoxyphenyl; and Q' and A are both ($C_1$–$C_4$)-straight chain alkyls substituted at the terminal end with a ($C_5$–$C_7$)-cycloalkyl, ($C_5$–$C_7$)-cycloalkenyl or Ar.

7. A compound of claim 2 wherein J and K are taken together to form a piperidine ring; the stereochemistry at carbon 1 is S; W is oxygen; m is 0; D is 3,4,5-trimethoxyphenyl; Q' is a ($C_5$–$C_7$)-cycloalkyl, ($C_5$–$C_7$)-cycloalkenyl or Ar; and A is a ($C_1$–$C_4$)-straight chain alkyl substituted at the terminal end with a ($C_5$–$C_7$)-cycloalkyl, ($C_5$–$C_7$)-cycloalkenyl or Ar.

8. A compound of claim 2 wherein J and K are taken together to form a pyrrolidine ring; the stereochemistry at carbon 1 is S; W is oxygen; m is 0; D is 3,4,5-trimethoxyphenyl; Q' is a ($C_5$–$C_7$)-cycloalkyl, ($C_5$–$C_7$)-cycloalkenyl or Ar; and A is a ($C_1$–$C_4$)-straight chain alkyl substituted at the terminal end with a ($C_5$–$C_7$)-cycloalkyl, ($C_5$–$C_7$)-cycloalkenyl or Ar.

9. A pharmaceutical composition which comprises as an active ingredient an amount of a compound as claimed in any one of claims 1, 2, and 5 to 8, or a pharmaceutically acceptable salt thereof, effective for stimulating neurite growth in nerve cells, and one or more pharmaceutically acceptable carriers, excipients or diluents thereof.

10. A method for stimulating neurite growth in nerve cells comprising the step of contacting said nerve cells with a composition comprising a neurotrophic amount of a compound with affinity for an FK-506 binding protein as claimed in any one of claims 1, 2 and 3–8.

11. A method for stimulating neurite growth in nerve cells comprising the step of contacting said nerve cells with a composition comprising a neurotrophic amount of a compound with affinity for FKBP12 as claimed in any one of claims 1, 2 and 5–8.

* * * * *